(12) United States Patent
Frye

(10) Patent No.: US 7,137,988 B2
(45) Date of Patent: Nov. 21, 2006

(54) NEEDLE DRIVER

(76) Inventor: Darrin L. Frye, 3594 S. Ocean Blvd., #601, Highland Beach, FL (US) 33487

(*) Notice: Subject to any disclaimer, the term of this patent is extended or adjusted under 35 U.S.C. 154(b) by 52 days.

(21) Appl. No.: 09/798,669

(22) Filed: Mar. 3, 2001

(65) Prior Publication Data

US 2002/0123757 A1   Sep. 5, 2002

(51) Int. Cl.
   *A61B 17/12* (2006.01)
(52) U.S. Cl. .......... 606/147; 606/144; 81/300
(58) Field of Classification Search .......... 606/144, 606/145, 147; 81/300, 317, 329, 342, 347; 112/169, 311
   See application file for complete search history.

(56) References Cited

U.S. PATENT DOCUMENTS

| | | | | |
|---|---|---|---|---|
| 89,016 A | * | 1/1869 | Howell | 606/207 |
| 3,834,021 A | * | 9/1974 | White et al. | 30/232 |
| 4,374,523 A | * | 2/1983 | Yoon | 606/141 |
| 4,449,518 A | * | 5/1984 | Konomura et al. | 600/133 |
| 4,646,751 A | * | 3/1987 | Maslanka | 600/564 |
| 4,990,152 A | * | 2/1991 | Yoon | 606/140 |
| 4,994,079 A | * | 2/1991 | Genese et al. | 606/206 |
| 5,201,739 A | * | 4/1993 | Semm | 606/106 |
| 5,334,209 A | * | 8/1994 | Yoon | 606/141 |
| 5,383,895 A | * | 1/1995 | Holmes et al. | 606/206 |
| 5,415,666 A | * | 5/1995 | Gourlay et al. | 606/142 |
| 5,499,997 A | * | 3/1996 | Sharpe et al. | 606/206 |
| 5,810,850 A | * | 9/1998 | Hathaway et al. | 606/144 |
| 5,830,125 A | * | 11/1998 | Scribner et al. | 606/139 |
| 5,830,232 A | * | 11/1998 | Hasson | 606/213 |
| 5,944,739 A | * | 8/1999 | Zlock et al. | 606/232 |
| 5,951,575 A | * | 9/1999 | Bolduc et al. | 606/144 |
| 6,149,642 A | * | 11/2000 | Gerhart et al. | 606/1 |
| 6,210,416 B1 | * | 4/2001 | Chu et al. | 606/113 |
| 6,280,458 B1 | * | 8/2001 | Boche et al. | 606/206 |

* cited by examiner

*Primary Examiner*—Henry Bennett

(57) ABSTRACT

An improved needle driver, wherein the needle driver includes an elongated body having a substantially hollow interior portion and a first and second ends. An actuator extending from the first end of the elongated body is included and is in communication with the substantially hollow interior portion. A selectively compressible air reservoir is included and positioned within the substantially hollow interior portion and is in communication with the actuator. A pair of mechanically actuated opposing jaw members extending from the second end of the elongated body into the substantially hollow interior portion are included, the pair of opposing jaw members are generally in communication with the actuator. An inflatable air reservoir is included and annularly positioned about the pair of opposing jaw members and is in communication with the selectively compressible air reservoir.

10 Claims, 5 Drawing Sheets

NEEDLE DRIVER

BACKGROUND OF THE INVENTION

1. Field of the Invention

The present invention relates to medical devices for securing and manipulating a suturing needle surgical procedures.

2. Background of the Related Art

Suturing is commonly known as the practice of using lengths of medical suture material to ligate or approximate tissue for proper healing after a surgical or other type of invasive medical procedure involving an incision. The process of suturing bodily tissue upon completion of medical procedure, whether the particular procedure is open, endoscopic, laproscopic, or another type of procedure, generally encompasses a substantial portion of the respective procedure time. In open-type surgical procedures, which refers to a procedure wherein the surgeon gains access to a surgical site via a relatively large incision, for example, the sutures required to properly ligate such an incision can easily take tens of minutes to properly and carefully apply. In endoscopic and/or laproscopictype procedures, which generally refers to minimally invasive-type surgerical procedures wherein the surgeon gains access to the surgical site via one or more small tissue portals/incisions, the suturing processes may be substantially more complicated, as the surgeon generally has a diminished view of an internal suturing site as well as a substantially reduced physical space for manipulating the respective suturing equipment. Therefore, the time required to suture in these internal-type situations is generally substantially longer than in open-type procedures, in addition to being substantially more difficult for the surgeon to accomplish.

In conventional medical techniques, suturing processes have generally been accomplished with the use of a sharp suture needle carrying a length of suture material, wherein the suture needle is caused to penetrate and pass through the tissue while simultaneously pulling the suture material therethrough. Once the suture material has been pulled through the tissue, the surgeon ties a knot in the suture material and secures the suture. Conventional needle drivers 100, an example of which is shown in FIG. 1, require the surgeon to grip the needle with the jaw portion 101 of needle driver 100, possibly locking jaws 101 in tension with a ratchet mechanism 103 in the handle 102 portion, and thereafter, manipulate the needle so as to create sutures. The surgeon may engage and control needle driver 100 via placement of the appropriate fingers within the respective handle finger holes 104.

However, a surgeon's manipulation of the conventional needle driver 100 is plainly limited by the physical configuration of the conventional needle driver 100. For example, as a result of the surgeon having at least one finger placed in finger holes 104, the surgeon's ability to manipulate/rotate the needle drover about a longitudinal axis of the needle driver 100 outside of approximately a 180° radius is prohibited, as movement beyond this range is not possible by the human arm. As such, movements at even a fraction of the possible 180° range often require the surgeon to go through odd and/or uncomfortable motions, such as elevation of the surgeon's elbow corresponding to the hand having the needle driver 100 therein upward in order to engage tissue with the needle. This process is known to cause strain and fatigue on a surgeon during suturing, and therefore, presents a potential for fatigue and/or strain based error. Additionally, the configuration of the jaws of conventional needle drivers results in the optimal gripping force being obtained when the jaws of the needle driver are completely closed. Inasmuch as a needle may not be gripped by the needle driver when the jaws are closed, as there is no physical space between the jaws in this position, conventional devices are note capable of gripping the needle with the optimal force available from the respective driver.

The shortcomings of conventional needle drivers are exacerbated when used in connection with microsurgery and endoscopic surgery, as these types of procedures require additional time and surgical effort to complete as a result of the nature of the surgical procedures. This can unduly prolong the duration of surgery, and therefore, prolong the period in which the patient is under anesthesia, which is undesired. Further, as a result of the less than optimal needle gripping force available from conventional devices, surgeons often have difficulty in maintaining a suture needle within the jaws of conventional devices, which may result in a needle drop. Nevertheless, endoscopic surgery is often preferred over open surgery due to the ability to reduce incision trauma and facilitate wound healing, which directly results in cost savings associated with shorter hospital stays and performing surgery in non-hospital and/or out-patient surgery sites.

Accordingly, there has a substantial effort develop apparatuses and methods for facilitating the suturing normally performed via a conventional needle driver. Alternative techniques have included electrical coagulation, mechanical clips, clamps and staples, electrical optical devices such as lasers, among other techniques. However, current innovation has generally failed to provide a needle driver capable of providing sufficient clamping force on the needle along with providing a configuration that minimizes surgical stress and fatigue on the surgeon. Current configurations also have failed to provide a needle driver that is able to rotate through at least 180° without awkward or stressful movements on behalf of the surgeon.

Therefore, in view of the deficiencies in conventional needle drivers in conjunction with the desirable characteristics of endoscopic and laproscopic techniques, there exists a need for an improved needle driver capable of providing a gripping force that is sufficient to maintain a surgical suture needle during a suturing process. Additionally, there exists a need for a needle driver that provides improved ergonomic characteristics over conventional devices so that the needle driver may be easily manipulated by the surgeon with minimal stress and/or fatigue. Further, there exists a need for a needle driver capable of being manipulated/rotated by the surgeon through a radius of at least 180°.

SUMMARY OF THE INVENTION

The present invention provides an improved needle driver, wherein the needle driver includes an elongated body having a substantially hollow interior portion and a first and second ends. An actuator extending from the first end of the elongated body is included and is in communication with the substantially hollow interior portion. A selectively compressible air reservoir is included and positioned within the substantially hollow interior portion and is in communication with the actuator. A pair of mechanically actuated opposing jaw members extending from the second end of the elongated body into the substantially hollow interior portion are included, the pair of opposing jaw members are generally in communication with the actuator. An inflatable air reservoir is included and annularly positioned about the pair of opposing jaw members and is in communication with the selectively compressible air reservoir.

The present invention farther provides an improved needle driver having a substantially hollow elongated body portion, the elongated body portion having a cylindrical exterior shape. A clamping device extending from a first end of the body portion is provided, the clamping device being biased to a first position. A longitudinal actuation member having an enlarged portion extending from a second end of the body portion is provided, the actuation member being in communication with the clamping device through the substantially hollow elongated body portion and being configured to actuate the clamping device to a second position.

BRIEF DESCRIPTION OF THE DRAWINGS

So that the manner in which the above recited features and embodiments are attained and can be understood in detail, a more particular description of the invention, briefly summarized above, may be had by reference to the embodiments thereof which are illustrated in the appended drawings. It is to be noted, however, that the appended drawings illustrate only typical and/or exemplary embodiments of the present invention, and are therefore, not to be considered limiting of its scope, as the invention may admit to other and/or alternative equally effective embodiments.

DETAILED DESCRIPTION OF THE PREFERRED EMBODIMENTS

Figure 1:
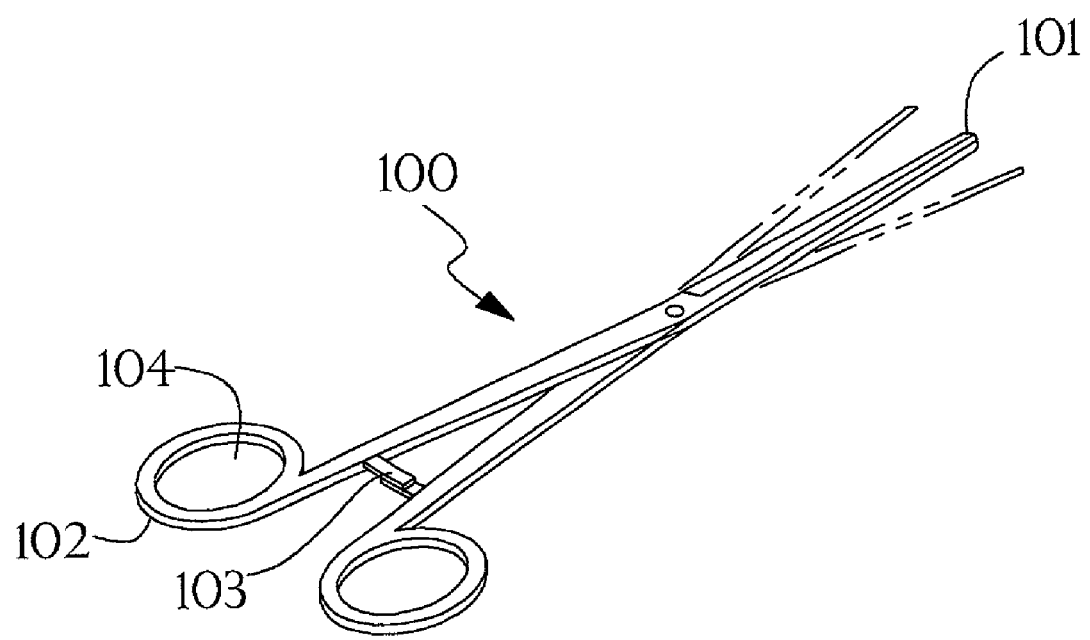
FIG. 1 illustrates a conventional needle driver.
Figure 2:
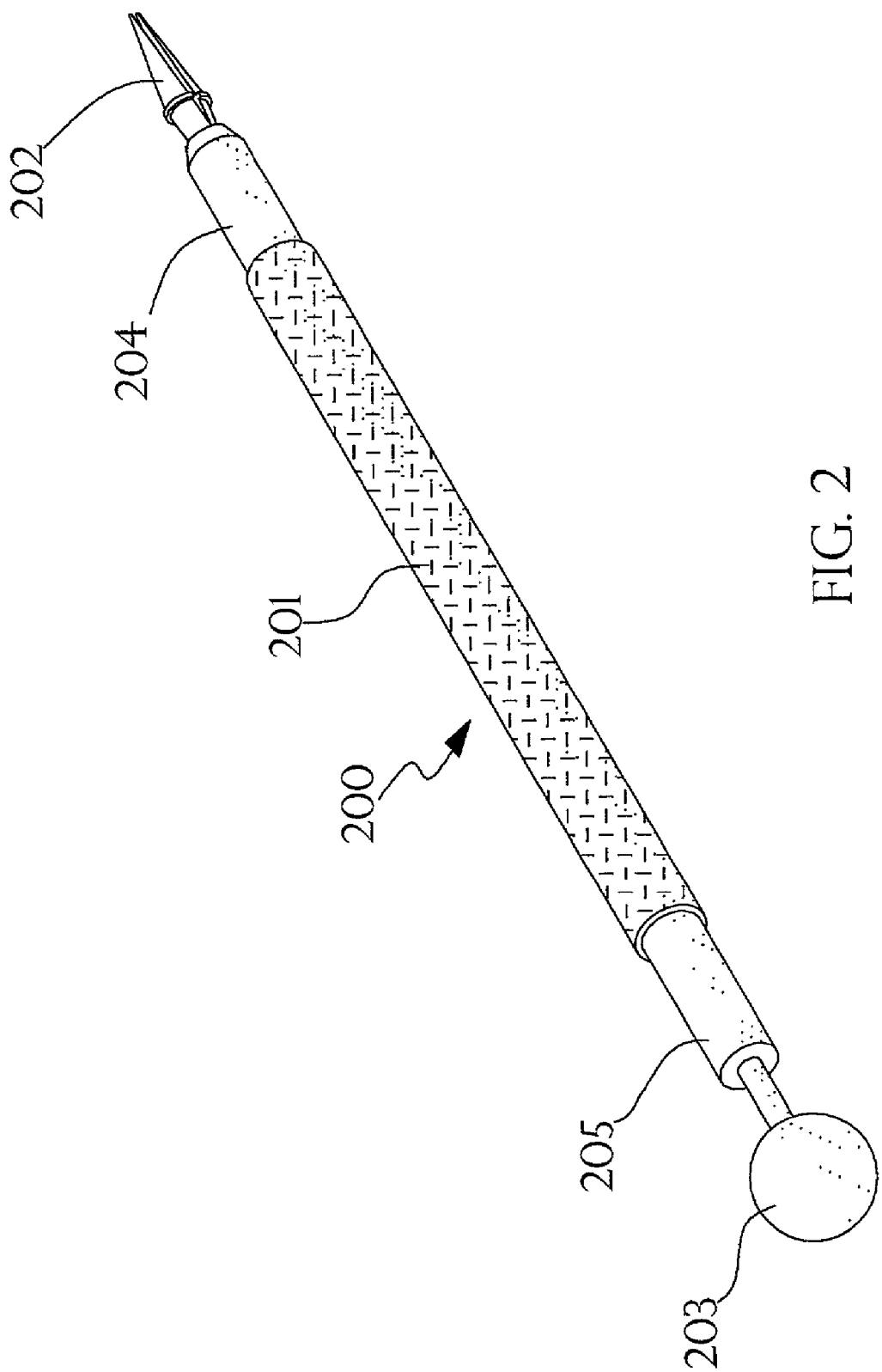
FIG. 2 illustrates an exemplary needle driver of the present invention.

FIG. 2 illustrates an exemplary needle driver of the present invention. Needle driver 200 generally includes an elongated body 201 having a substantially hollow interior portion. A pair of jaw members 202 longitudinally extend from a first end 204 of elongated body 201. An actuation member 203 longitudinally extends from a second end 205 of elongated body 201 and includes and enlarged end portion. Actuation member 203 is in communication with at least one of jaw members 202 via a mechanical connection longitudinally extending through the substantially hollow interior portion of elongated body 201. Therefore, when actuation member 203 is longitudinally actuated by the user, jaw members 202 are mechanically caused to close, and therefore, grip a needle placed therebetween. Elongated body is generally configured with a surface that facilitates gripping of the needle driver by the user. Further, when the outer housing is rotated by the user, the jaw members 202 may be configured to rotate therewith.

Figure 3:
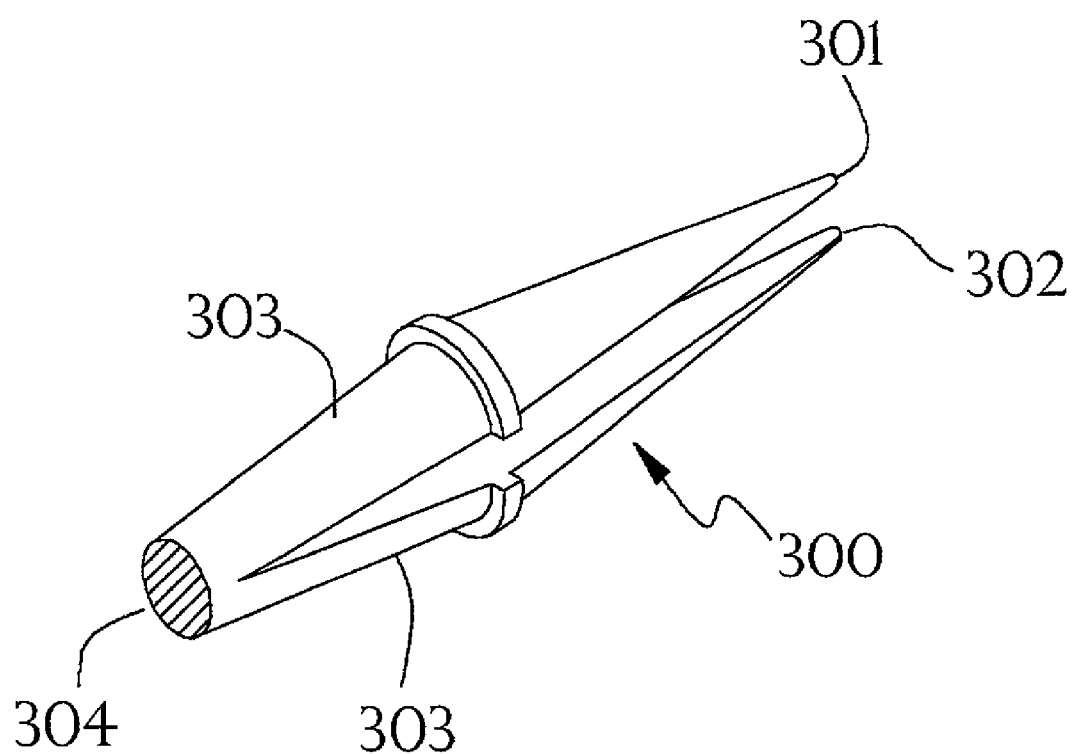
FIG. 3 illustrates an exemplary configuration of jaw members.

The jaw member of a needle driver of the present invention may be configured, for example, as a unitary piece, as shown in FIG. 3. The exemplary jaw member 300 includes a first side 301 and a second side 302, wherein the respective sides are interconnected via a common base 304. As a result of the interconnection, first side 301 is biased away from second side 302 in a spring like manner. This bias condition is generally configured to separate first side 301 from second side 302 a sufficient distance to allow a needle to be placed therebetween. Once a needle is placed between first side 301 and second side 302, jaw member may be actuated and closed to secure the needle between the respective sides.

The process of closing the exemplary jaw member 300 generally involves moving jaw member 300 in a longitudinal direction. For example, once a needle is placed between the first and second sides, the exemplary jaw member may be drawn towards the body portion of the needle driver, which is generally annularly positioned about the base end of jaw member 300. When jaw member 300 is drawn into the end of the body, inclined regions 303 may be caused to slidably engage corresponding inclined regions positioned about the interior of the body portion. As a result of this slidable engagement, which resembles two wedges sliding along their respective wedge surfaces, first side 301 and second side 302 of jaw member 300 are caused to move proximate to each other, thereby securing a needle therebetween. Jaw member 300 may be caused to longitudinally move via a mechanical connection with an actuator, such as, a mechanical rod, for example.

Alternatively, jaw member 300 may be configured to operate in an opposite manner by reversing the slope of the inclined surfaces. For example, if inclined surfaces 303 were reversed, then first side 301 and second side 302 may be caused to come together via actuation of jaw member 300 in a direction away from a needle driver body portion. As such, a needle driver of the present invention may be configured to close and grip a needle upon actuation of an actuating member along the longitudinal axis of the needle driver in either direction.

Furthermore, although jaw member 300 is disclosed as a unitary jaw member, the present invention contemplates various alternative jaw configurations within the scope of the present invention. For example, a pair of jaw members may include a stationary jaw member cooperatively operating with a pivotally mounted jaw member, wherein the pivotally mounted jaw member is caused to pivot towards the stationary member in order to secure a needle between the respective members. Alternatively, both jaw members may be pivotally mounted and caused to pivot towards each other in order to secure a needle therebetween.

Irrespective of the jaw configuration utilized, the overall shape of a needle driver of the present invention is generally cylindrical in shape, for example, in similar fashion to an ink pen. Generally, the largest diameter of a needle driver of the present invention is an actuation member. The remainder of the needle driver generally resembles an elongated cylindrical body, which may be manufactured to essentially any length, having a pair of jaws extending therefrom. The pair of jaws are generally of a lesser diameter than the body and the actuation member. As a result of this configuration, the needle driver of the present invention may generally be held in a surgeon's hand with the actuation member resting against the base of the palm and the body portion being engaged by at least two fingers. Therefore, when the surgeon desires to grip a needle with the jaws of the needle driver, the needle driver need only be moved along the longitudinal axis. This movement may be caused by using the fingers to move the needle driver into the hand, which causes the actuation member to become in abutment with the surgeon's palm, and therefore, actuate the jaw portion to grip a needle. Alternatively, the actuation member may be secured with the little finger of the surgeon by wrapping the little finger around the actuation member. In this configuration, the surgeon may use the remaining fingers to pull the needle driver away from the palm, which again may longitudinally actuate the jaw members to either grip or release a needle. Regardless of the direction of travel needed in order to close the jaw members, the actuation is generally biased via a spring, for example, positioned within the needle driver. This bias allows the jaw portions, as well as the actuation member, to return to a predictable position when no force is applied to the actuation member. Therefore, the operation of needle driver in the unactuated position is predictable.

Figure 4:
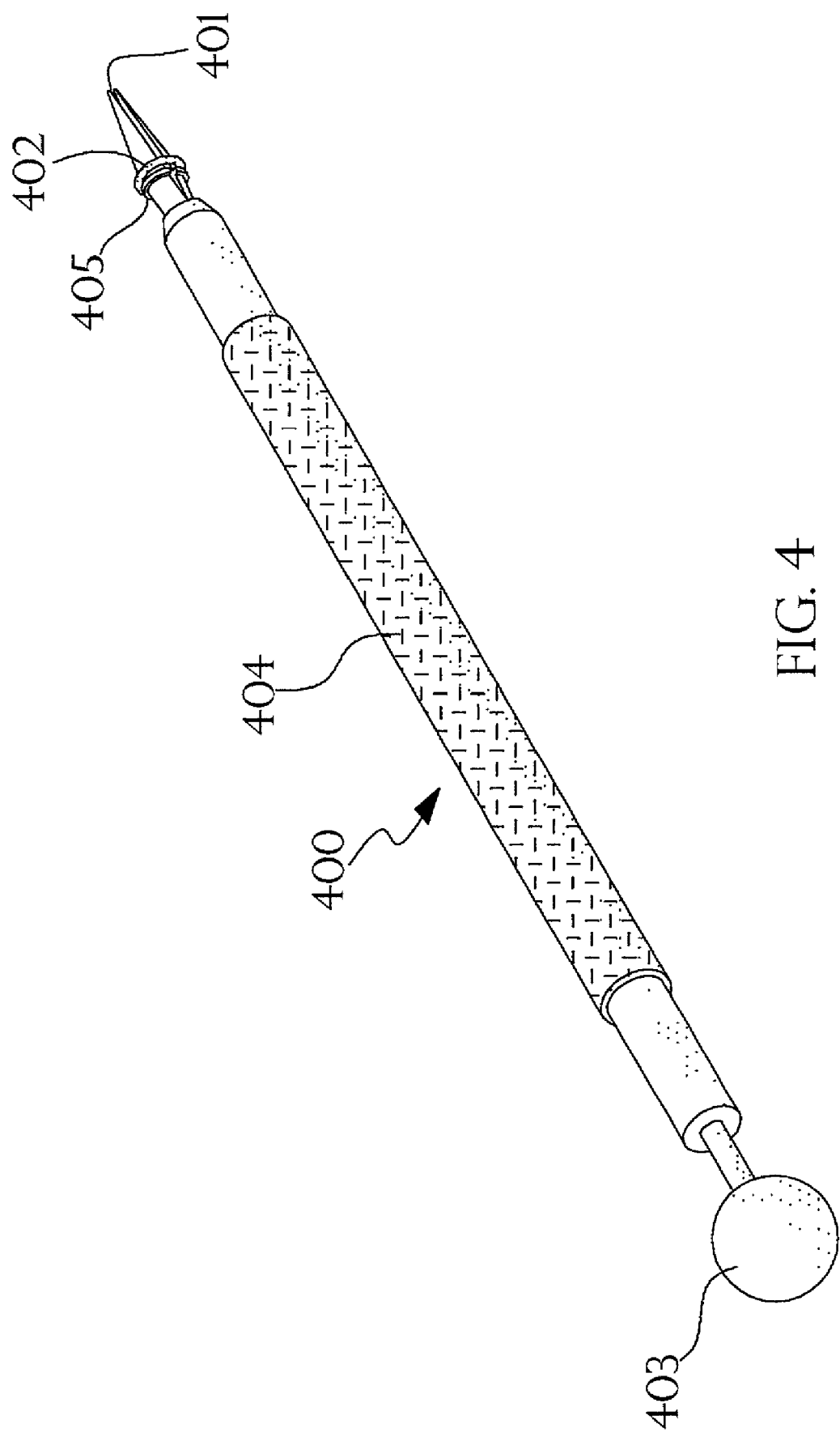
FIG. 4 illustrates a conventional needle driver with an annular tension ring.

FIG. 4 illustrates another exemplary embodiment of a needle driver of the present invention. Needle driver 400 may be structurally similar to the needle driver illustrated in FIG. 2, however, needle driver 400 includes an additional structural feature designed to provide additional gripping force to jaws 401. Needle driver 400 includes an elongated body member 404 having an actuating member 403 extending from one end and a pair of opposing jaw members 401 extending from the other end. In similar fashion to previous embodiments, jaw members 401 may be actuated through longitudinal movement of actuating member 403, wherein the longitudinal meo0vement may once again be in either direction, depending upon the particular jaw configuration employed. However, needle driver 400 includes an inflatable annular ring 402 positioned about a base portion of jaw members 401 for providing additional gripping force to jaw members 401. Inflatable ring 402 may be caused to inflate upon longitudinal movement of actuation member 403. Therefore, when a surgeon actuates the actuation member 403 to close jaw members 401, inflatable ring is simultaneously caused to inflate and exert an additional closing force on jaw members 401.

Inflatable annular ring 402 may be manufactured from a rubber or poly product, or other similar material. Annular ring 402 is generally configured to maintain an inside diameter when not inflated, which allows annular ring to stay positioned on jaw members 401 when not inflated. Additionally, annular ring 402 may be configured to maintain its ring like shape when not inflated. Upon inflation, ring 402 may be configured to generally maintain a relatively constant outside diameter while reducing its inside diameter. Therefore, upon inflation, ring 402 may generally maintain the same outer profile, while expanding/inflating inwardly, which exerts an inward force upon jaw members 401. This additional force may operate to further secure a needle within jaw members 401, which in turn reduces the possibility of dropping the needle, in addition to reducing surgeon fatigue resulting from constant gripping of the needle with the needle driver.

Figure 5:
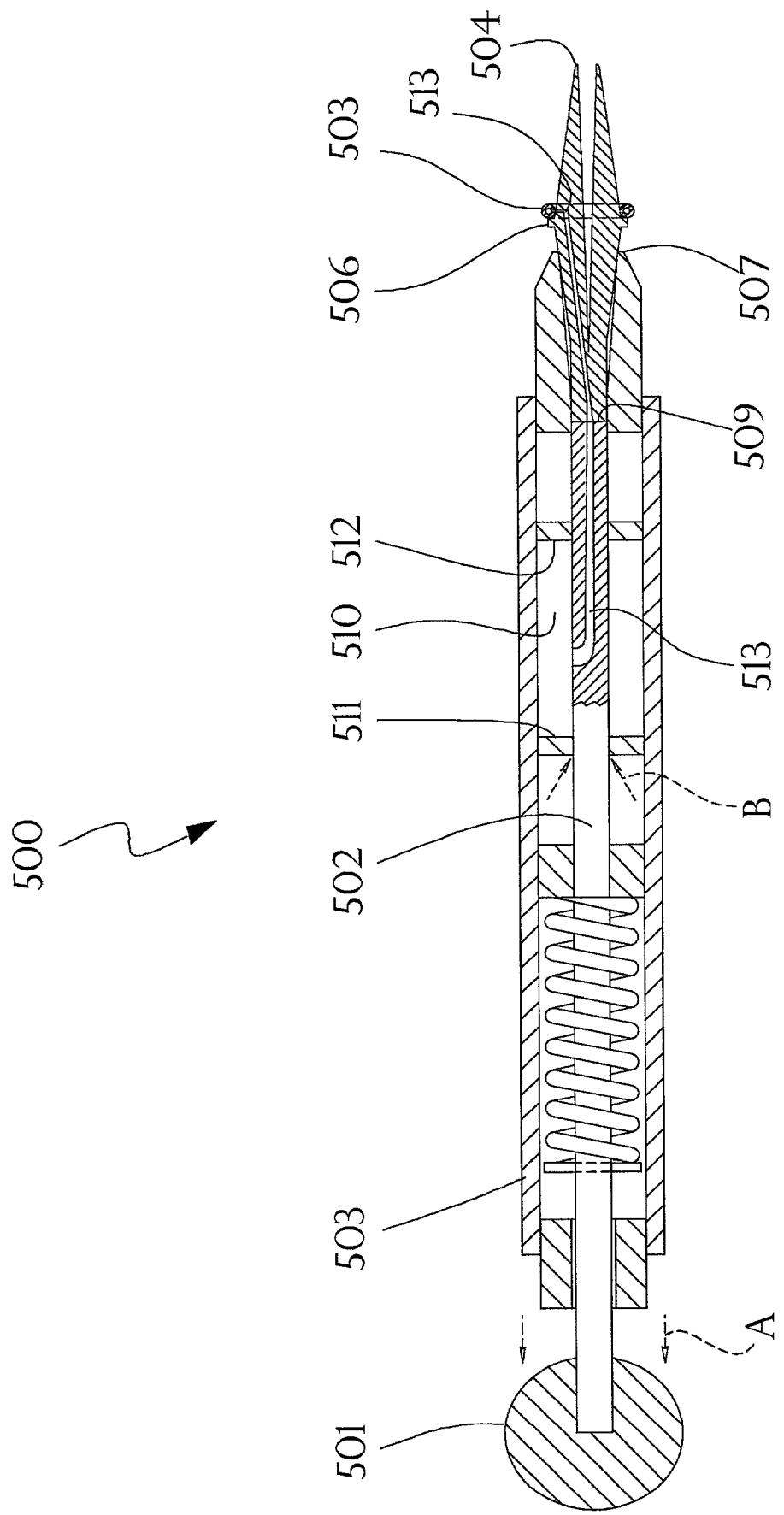
FIG. 5 illustrates a sectional view of an exemplary needle driver of the present invention.

FIG. 5 illustrates a sectional view of an exemplary embodiment of the present invention. Needle driver 500 includes an actuation member 501 in communication with a longitudinal actuation rod 502 that is positioned within a substantially hollow interior portion of an elongated body member 503. Actuation rod 502 is mechanically connected to a base portion 509 of a unitary jaw member 504. Therefore, in this exemplary configuration, when a surgeon causes actuation member 501 to travel in the direction indicated by arrow "A," inclined surfaces 507 on jaw member 504 slidably engage a wedge members 508 positioned within the end of elongated body 503. This slidable engagement causes jaw members 504 to close as a result of the wedge engagement.

Simultaneously with wedge members 508 causing jaw members 504 to close, annular ring 505 positioned near the base 506 of jaw members 504 may be caused to inflate and provide an additional gripping force to jaw members 504. Annular ring 505 may be caused to inflate via air pressure supplied Thereto through an air passage 513, which is in fluid communication with annular ring 505. Air passage 513 is generally in communication with a compressible air chamber 510. Chamber 510 may be configured to supply air to air passage 513 upon longitudinal movement of actuation rod 502.

In the present exemplary embodiment, for example, a pair of valves 511, 512 may be concentrically positioned about actuation rod 502. In this exemplary configuration, first valve 511 may be fixed to the interior wall of elongated body 503 with a first side while slidably engaging actuation rod 502 with a second side. Second valve 512 may be fixed to actuation rod 502 while slidably engaging in interior wall of elongated body 503. As such, valves 511 and 512 may be configured to create a bellows and/or compressible air chamber for providing air to inflate annular ring 505 when the needle driver is actuated. In the exemplary embodiment shown in FIG. 5, valve 511 may be configured to allow air to travel between actuation rod 502 and valve 511 in the direction indicated by arrow "B." Valve 512 may be configured to create a generally air tight seal between both actuation rod 502 and the inner wall of elongated body 503. Therefore, when actuation rod is moved in a direction opposite to arrow "A," jaws 504 will open and air will be drawn into air chamber 510 by the movement of valve 512. The air drawn into chamber 510 generally travels by valve 511 in the direction of arrow "B." When the actuation rod 502 is moved in the direction of arrow "A," the jaw members 504 are caused to close and grip, for example, a needle placed between jaw members 504 as a result of the engagement of inclined surfaces 507 with wedge members 508. Simultaneously with the closing of jaw members 504, valve 511 slidably engages actuation rod 502, but does not allow air to pass thereby. As such, the air within air chamber 510 is compressed and caused to flow into air passage 513, which may be in communication with air passage 510 via a bore formed in actuating rod 502. This air flow causes annular ring 505 to inflate, which operates to exert an additional clamping force on jaws 504.

With particularity, for example, the end of actuation rod 502 proximate jaw members 504 may have a hollow interior portion for communicating air through. This hollow interior portion may be in communication with air chamber 510 via a bore formed in the side of actuation rod 502. The hollow interior portion of actuation rod 502 may also be in communication with the air passage 513, which may be formed into the unitary jaw member 504. Therefore, when actuation rod is caused to move in the direction of arrow "A," the volume of chamber 510 is compressed. This may cause air in chamber 510 to flow into the substantially hollow interior portion of actuating rod 502 and into air passage 513. Since air passage 513 may be in communication with annular ring 505, the ring may be caused to inflate and exert an additional clamping force on jaw members 504 positioned within the annulus of the ring 505.

In an alternative embodiment, a compressible air chamber may be in communication with an inflatable annular ring positioned about a jaw member via an air passage formed in the wall of an outer casing for the needle driver. Also, a compressible air chamber may be formed into the jaw member itself, thereby eliminating the need to communicate air from a compressible air chamber to the jaw member. As such, the present invention contemplates various known methods for generating air pressure sufficient to inflate an annular ring sized to fit over a needle driver.

Further, although the present invention has been described with respect to specific exemplary embodiments, the present invention is not limited to the embodiments presented herein. For example, various clamping mechanisms may be incorporated into the present invention without departing from the true scope thereof. Further, the various clamping mechanisms may be actuated through various longitudinal actuators in various actuation directions.

While the foregoing is directed to the preferred embodiment of the present invention, other and further embodiments of the invention may be devised without departing from the basic scope thereof, and the scope thereof is determined by the claims that follow.

What is claimed is:

1. An improved needle driver, comprising:
   an elongated body having a substantially hollow interior portion and a first and second ends;
   an actuator extending from the first end of the elongated body and being in communication with the substantially hollow interior portion;
   a selectively compressible air reservoir positioned within the substantially hollow interior portion and being in communication with the actuator;
   a pair of mechanically actuated opposing jaw members extending from the second end of the elongated body into the substantially hollow interior portion, the pair of opposing jaw members being in communication with the actuator; and
   an inflatable air reservoir annularly positioned about the pair of opposing jaw members and being in communication with the selectively compressible air reservoir.

2. The improved needle driver of claim 1, wherein the inflatable air reservoir further comprises an annularly shaped inflatable member, wherein the inflatable member is configured to expand inwardly upon inflation thereof.

3. The improved needle driver of claim 1, wherein the selectively compressible air reservoir further comprises:
   an air chamber positioned within the elongated body; and
   a first and second valves defining a first and second ends of the air chamber,
   wherein the first and second valves are configured to transmit air from the air chamber to the inflatable reservoir upon longitudinal movement of the actuator.

4. The improved needle driver of claim 1, wherein the pair of mechanically actuated opposing jaw members further comprises a unitary clamping member having a first and second opposing jaw members biased away from each other.

5. The improved needle driver of claim 4, wherein the unitary clamping member further includes an inclined surface formed on an exterior portion of the unitary clamping member, the inclined surface being configured to slidably engage a wedge surface positioned on an interior wall of the second end of the elongated body.

6. An improved needle driver, comprising:
   a substantially hollow elongated body portion, the elongated body portion having a cylindrical exterior shape;
   a clamping device extending from a first end of the body portion, the clamping device being biased to a first position; and
   a longitudinal actuation member having an enlarged portion extending from a second end of the body portion, the actuation member being in communication with the clamping device through the substantially hollow elongated body portion and being configured to actuate the clamping device to a second position; and
   a selectively inflatable ring annularly positioned about the clamping device, the inflatable annular ring being configured to exert an additional clamping, force on the clamping device.

7. The improved needle driver of claim 6, further comprising a compressible air chamber in mechanical engagement with the actuation member, the compressible air chamber being configured to provide air to the annular ring upon actuation of the actuation member.

8. The improved needle driver of claim 7, wherein the compressible air chamber further comprises an annularly shaped chamber positioned within the substantially hollow elongated body portion, the compressible air chamber being defined on a first end by a first valve and on a second end by a second valve, one of the first and second valves being configured to allow air to pass thereby in a first direction but not a second direction, and another of the first and second valves being configured to not allow air to pass thereby in either the first or second direction.

9. The improved needle driver of claim 6, wherein the clamping device further comprises a unitary clamping member comprising:
   a first jaw member;
   a second jaw member positioned opposing the first jaw member;
   a base member interconnecting the first and second jaw members; and
   an inclined region positioned about an exterior portion of both the first and second jaw members, the inclined region being configured to slidably engage a wedge member positioned within the substantially hollow elongated body portion in order to
   actuate the first and second jaw members from the first position to the second position.

10. An improved needle driver, comprising:
    an elongated body having a substantially hollow interior portion and a first and second ends;
    a pair of mechanically actuated opposing jaw members extending from the second end of the elongated body into the substantially hollow interior portion; means for actuating the pair of opposing jaw members; and
    means for providing an additional actuating force to the pair of opposing jaw members, comprising selectively compressible air reservoir,positioned within the substantially hollow interior portion and being in communication with the actuating means; and an inflatable air reservoir annularly positioned about the pair of opposing jaw members and being in communication with the selectively compressible air reservoir.

* * * * *